(12) United States Patent
McGuckin, Jr.

(10) Patent No.: US 9,901,350 B2
(45) Date of Patent: Feb. 27, 2018

(54) CLOSURE DEVICE FOR LEFT ATRIAL APPENDAGE

(71) Applicant: James F. McGuckin, Jr., Radnor, PA (US)

(72) Inventor: James F. McGuckin, Jr., Radnor, PA (US)

(73) Assignee: Rex Medical, L.P., Conshohocken, PA (US)

( * ) Notice: Subject to any disclaimer, the term of this patent is extended or adjusted under 35 U.S.C. 154(b) by 196 days.

(21) Appl. No.: 14/280,459

(22) Filed: May 16, 2014

(65) Prior Publication Data

US 2014/0257365 A1     Sep. 11, 2014

Related U.S. Application Data

(62) Division of application No. 11/393,539, filed on Mar. 30, 2006, now Pat. No. 8,740,934.

(60) Provisional application No. 60/674,321, filed on Apr. 22, 2005.

(51) Int. Cl.
*A61B 17/12* (2006.01)
*A61B 17/00* (2006.01)

(52) U.S. Cl.
CPC .. *A61B 17/12122* (2013.01); *A61B 17/12022* (2013.01); *A61B 17/12145* (2013.01); *A61B 17/12172* (2013.01); *A61B 17/0057* (2013.01); *A61B 2017/00641* (2013.01); *A61B 2017/12095* (2013.01)

(58) Field of Classification Search
CPC ........ A61B 17/12022; A61B 17/12027; A61B 17/12031; A61B 17/12036; A61B 17/12122; A61B 17/12109; A61B 17/12113; A61B 17/12131; A61B 17/12136; A61B 17/0057; A61B 2017/00575

See application file for complete search history.

(56) References Cited

U.S. PATENT DOCUMENTS

| | | |
|---|---|---|
| 3,527,223 A | 9/1970 | Shein |
| 3,874,388 A | 4/1975 | King et al. |
| 3,958,576 A | 5/1976 | Komiya |
| 4,007,746 A | 2/1977 | Blake |
| 4,031,569 A | 6/1977 | Jacob |
| 4,317,445 A | 3/1982 | Robinson |
| 4,485,816 A | 12/1984 | Krumme |
| 4,505,274 A | 3/1985 | Speelman |
| 4,512,338 A | 4/1985 | Balko et al. |
| 4,610,671 A | 9/1986 | Luther |
| 4,665,906 A | 5/1987 | Jervis |
| 4,676,245 A | 6/1987 | Eukuda |

(Continued)

FOREIGN PATENT DOCUMENTS

| | | |
|---|---|---|
| DE | 19604817 | 8/1997 |
| EP | 0637431 | 2/1995 |

(Continued)

*Primary Examiner* — Dianne Dornbusch
(74) *Attorney, Agent, or Firm* — Neil D. Gershon

(57) ABSTRACT

A device for closing a left atrial appendage of a patient comprising a containment member having a first configuration for passage into the left atrial appendage and a second larger configuration, and a wire movable into the containment member in situ to expand the containment member in the left atrial appendage to the second configuration.

17 Claims, 10 Drawing Sheets

(56) References Cited

U.S. PATENT DOCUMENTS

| | | | |
|---|---|---|---|
| 4,744,364 A | 5/1988 | Kensey | |
| 4,917,089 A | 4/1990 | Sideris | |
| 4,924,866 A | 5/1990 | Yoon | |
| 4,971,068 A | 11/1990 | Sahi | |
| 5,021,059 A | 6/1991 | Kensey et al. | |
| 5,047,047 A | 9/1991 | Yoon | |
| 5,061,274 A | 10/1991 | Kensey | |
| 5,108,420 A | 4/1992 | Marks | |
| 5,171,252 A | 12/1992 | Friedland | |
| 5,171,259 A | 12/1992 | Inoue | |
| 5,192,300 A | 3/1993 | Fowler | |
| 5,192,301 A | 3/1993 | Kamilya et al. | |
| 5,192,302 A | 3/1993 | Kensey et al. | |
| 5,222,974 A | 6/1993 | Kensey et al. | |
| 5,246,441 A | 9/1993 | Ross et al. | |
| 5,279,572 A | 1/1994 | Hokama | |
| 5,282,827 A | 2/1994 | Kensey et al. | |
| 5,306,254 A | 4/1994 | Nash et al. | |
| 5,312,435 A | 5/1994 | Nash et al. | |
| 5,334,210 A * | 8/1994 | Gianturco | A61B 17/12022 604/907 |
| 5,350,399 A | 9/1994 | Erlebacher et al. | |
| 5,350,400 A | 9/1994 | Esposito et al. | |
| 5,385,554 A | 1/1995 | Brimhall | |
| RE34,866 E | 2/1995 | Kensey et al. | |
| 5,391,183 A | 2/1995 | Janzen et al. | |
| 5,411,520 A | 5/1995 | Nash et al. | |
| 5,443,481 A | 8/1995 | Lee | |
| 5,451,235 A | 9/1995 | Lock et al. | |
| 5,474,557 A | 12/1995 | Mai | |
| 5,478,352 A | 12/1995 | Fowler | |
| 5,478,353 A | 12/1995 | Yoon | |
| 5,486,195 A | 1/1996 | Myers et al. | |
| 5,531,759 A | 7/1996 | Kensey et al. | |
| 5,540,716 A | 7/1996 | Hlavacek | |
| 5,545,178 A | 8/1996 | Kensey et al. | |
| 5,549,633 A | 8/1996 | Evans et al. | |
| 5,591,204 A | 1/1997 | Janzen et al. | |
| 5,593,422 A | 1/1997 | Muijs Van de Moer et al. | |
| 5,620,461 A | 4/1997 | Muijs Van de Moer et al. | |
| 5,630,833 A | 5/1997 | Katsaros et al. | |
| 5,634,936 A * | 6/1997 | Linden | A61B 17/0057 604/60 |
| 5,643,317 A | 7/1997 | Pavcnik et al. | |
| 5,649,959 A | 7/1997 | Hannam et al. | |
| 5,662,681 A | 9/1997 | Nash et al. | |
| 5,674,231 A | 10/1997 | Green et al. | |
| 5,676,689 A | 10/1997 | Kensey et al. | |
| 5,683,411 A | 11/1997 | Kavteladze | |
| 5,690,674 A | 11/1997 | Diaz | |
| 5,700,277 A | 12/1997 | Nash et al. | |
| 5,702,421 A | 12/1997 | Schneidt | |
| 5,709,707 A | 1/1998 | Lock et al. | |
| 5,725,498 A | 3/1998 | Janzen et al. | |
| 5,728,132 A | 3/1998 | Van Tassel et al. | |
| 5,728,133 A | 3/1998 | Kontos | |
| 5,741,297 A | 4/1998 | Simom | |
| 5,782,844 A | 7/1998 | Yoon et al. | |
| 5,782,860 A | 7/1998 | Epstein et al. | |
| 5,782,861 A | 7/1998 | Cragg et al. | |
| 5,810,846 A | 9/1998 | Vimich et al. | |
| 5,810,851 A | 9/1998 | Yoon | |
| 5,810,884 A | 9/1998 | Kim | |
| 5,820,628 A | 10/1998 | Middleman et al. | |
| 5,846,261 A | 12/1998 | Kotula et al. | |
| 5,861,003 A * | 1/1999 | Latson | A61B 17/0057 606/157 |
| 5,893,856 A | 4/1999 | Jacob et al. | |
| 5,910,155 A | 6/1999 | Ratcliff et al. | |
| 5,916,236 A | 6/1999 | Muijs Van de Moer et al. | |
| 5,919,207 A | 7/1999 | Taheri | |
| 5,964,782 A | 10/1999 | Lafontaine et al. | |
| 5,976,159 A | 11/1999 | Bolduc et al. | |
| 5,976,174 A * | 11/1999 | Ruiz | A61B 17/0057 606/151 |
| 5,984,949 A | 11/1999 | Levin | |
| 6,001,110 A | 12/1999 | Adams | |
| 6,007,563 A | 12/1999 | Nash et al. | |
| 6,015,417 A | 1/2000 | Reynolds | |
| 6,033,427 A | 3/2000 | Lee | |
| 6,048,357 A | 4/2000 | Kontos | |
| 6,048,358 A | 4/2000 | Barak | |
| 6,056,768 A | 5/2000 | Cates et al. | |
| 6,063,085 A | 5/2000 | Tay et al. | |
| 6,071,300 A | 6/2000 | Brenneman et al. | |
| 6,077,281 A | 6/2000 | Das | |
| 6,080,182 A | 6/2000 | Shaw et al. | |
| 6,080,183 A | 6/2000 | Tsugita et al. | |
| 6,086,577 A | 7/2000 | Ken et al. | |
| 6,113,611 A | 9/2000 | Allen et al. | |
| 6,117,159 A | 9/2000 | Huebsch et al. | |
| 6,120,524 A | 9/2000 | Taheri | |
| 6,139,564 A | 10/2000 | Teoh | |
| 6,152,144 A * | 11/2000 | Lesh | A61B 17/0057 128/898 |
| 6,171,320 B1 | 1/2001 | Monassevitch | |
| 6,171,329 B1 | 1/2001 | Shaw et al. | |
| 6,174,322 B1 | 1/2001 | Schneidt | |
| 6,179,863 B1 | 1/2001 | Kensey | |
| 6,193,708 B1 * | 2/2001 | Ken | A61B 17/12022 606/1 |
| 6,197,042 B1 | 3/2001 | Ginn et al. | |
| 6,206,907 B1 | 3/2001 | Marino et al. | |
| 6,228,096 B1 | 5/2001 | Marchand | |
| 6,231,561 B1 | 5/2001 | Frazier et al. | |
| 6,251,122 B1 | 6/2001 | Tsukernik | |
| 6,261,309 B1 | 7/2001 | Urbanski | |
| 6,277,140 B2 | 8/2001 | Ginn et al. | |
| 6,328,727 B1 | 12/2001 | Frazier et al. | |
| 6,334,865 B1 | 1/2002 | Redmond et al. | |
| 6,336,914 B1 | 1/2002 | Gillespie | |
| 6,342,064 B1 | 1/2002 | Koike et al. | |
| 6,346,117 B1 * | 2/2002 | Greenhalgh | A61B 17/12022 606/200 |
| 6,350,270 B1 * | 2/2002 | Roue | A61B 17/12022 606/151 |
| 6,350,274 B1 | 2/2002 | Li | |
| 6,355,052 B1 | 3/2002 | Neuss | |
| 6,368,341 B1 | 4/2002 | Abrahamson | |
| 6,375,668 B1 * | 4/2002 | Gifford | A61B 17/12022 606/200 |
| 6,391,048 B1 | 5/2002 | Ginn et al. | |
| 6,409,739 B1 | 6/2002 | Nobels et al. | |
| 6,419,669 B1 | 7/2002 | Frazier et al. | |
| 6,425,911 B1 | 7/2002 | Akerfeldt et al. | |
| 6,436,088 B2 | 8/2002 | Frazier et al. | |
| 6,447,524 B1 | 9/2002 | Knodel et al. | |
| 6,482,179 B1 | 11/2002 | Chu et al. | |
| 6,488,689 B1 | 12/2002 | Kaplan et al. | |
| 6,508,828 B1 | 1/2003 | Akerfeldt et al. | |
| 6,511,468 B1 | 1/2003 | Cragg et al. | |
| 6,537,299 B1 | 3/2003 | Hogendijk et al. | |
| 6,551,303 B1 * | 4/2003 | Van Tassel | A61B 17/12022 128/898 |
| 6,569,185 B2 | 5/2003 | Ungs | |
| 6,585,748 B1 * | 7/2003 | Jeffree | A61B 17/12022 606/200 |
| 6,596,012 B2 | 7/2003 | Akerfeldt et al. | |
| 6,626,937 B1 | 9/2003 | Cox | |
| 6,652,555 B1 | 11/2003 | Van Tassel et al. | |
| 6,652,556 B1 * | 11/2003 | VanTassel | A61B 17/12122 606/200 |
| 6,682,489 B2 | 1/2004 | Tenerz et al. | |
| 6,689,150 B1 | 2/2004 | Van Tassel et al. | |
| 6,712,837 B2 | 3/2004 | Akerfeldt et al. | |
| 6,730,108 B2 | 5/2004 | Van Tassel et al. | |
| 6,749,621 B2 | 6/2004 | Pantages et al. | |
| 6,749,622 B2 | 6/2004 | McGuckin, Jr. et al. | |
| 6,766,186 B1 | 7/2004 | Hoyns et al. | |
| 6,790,220 B2 | 9/2004 | Morris | |
| 6,949,107 B2 | 9/2005 | McGuckin, Jr. et al. | |
| 6,949,113 B2 | 9/2005 | Van Tassel et al. | |
| 6,960,224 B2 | 11/2005 | Marino et al. | |

(56) References Cited

U.S. PATENT DOCUMENTS

| | | |
|---|---|---|
| 6,994,092 B2 | 2/2006 | Van der Burg et al. |
| 7,025,776 B1 | 4/2006 | Houser et al. |
| 7,033,393 B2 | 4/2006 | Gainor et al. |
| 7,153,323 B1* | 12/2006 | Teoh ................ A61B 17/12022 606/158 |
| 2002/0082622 A1 | 6/2002 | Kane |
| 2002/0111647 A1* | 8/2002 | Khairkhahan ..... A61B 17/0057 606/200 |
| 2003/0009180 A1 | 1/2003 | Hinchliffe et al. |
| 2003/0055450 A1 | 3/2003 | Jones et al. |
| 2003/0055451 A1 | 3/2003 | Jones et al. |
| 2003/0088269 A1 | 5/2003 | Ashby |
| 2003/0105487 A1 | 6/2003 | Bemz et al. |
| 2003/0144695 A1 | 7/2003 | McGuckin, Jr. et al. |
| 2004/0002764 A1 | 1/2004 | Gainor et al. |
| 2004/0098031 A1* | 5/2004 | van der Burg ..... A61B 17/0057 606/200 |
| 2004/0098042 A1* | 5/2004 | Devellian .......... A61B 17/0057 606/213 |
| 2004/0143294 A1 | 7/2004 | Corcoran et al. |
| 2004/0158287 A1 | 8/2004 | Cragg et al. |
| 2004/0220610 A1* | 11/2004 | Kreidler ............ A61B 17/0057 606/200 |
| 2005/0033326 A1 | 2/2005 | Briganti et al. |
| 2005/0043759 A1* | 2/2005 | Chanduszko ...... A61B 17/0057 606/213 |
| 2005/0065547 A1 | 3/2005 | Marino et al. |
| 2005/0070957 A1 | 3/2005 | Das |
| 2005/0090859 A1 | 4/2005 | Ravlkumar |
| 2005/0107807 A1 | 5/2005 | Nakao |
| 2005/0113861 A1* | 5/2005 | Corcoran ........... A61B 17/0057 606/200 |
| 2005/0177182 A1* | 8/2005 | van der Burg ..... A61B 17/0057 606/157 |
| 2005/0192627 A1 | 9/2005 | Whisenant et al. |
| 2005/0267524 A1 | 12/2005 | Chanduszko |
| 2006/0106418 A1 | 5/2006 | Seibold et al. |
| 2006/0155327 A1 | 7/2006 | Briganti et al. |

FOREIGN PATENT DOCUMENTS

| | | |
|---|---|---|
| EP | 0920842 | 6/1999 |
| WO | 95/20916 | 8/1995 |
| WO | 9707741 | 3/1997 |
| WO | 9827868 | 7/1998 |
| WO | 99/03404 | 1/1999 |
| WO | 9900055 | 1/1999 |
| WO | 9905977 | 2/1999 |
| WO | 1999/30640 | 6/1999 |
| WO | 9938454 | 8/1999 |
| WO | 01/30266 | 5/2001 |
| WO | 2008/150346 | 12/2008 |
| WO | 2010/056535 | 5/2010 |

* cited by examiner

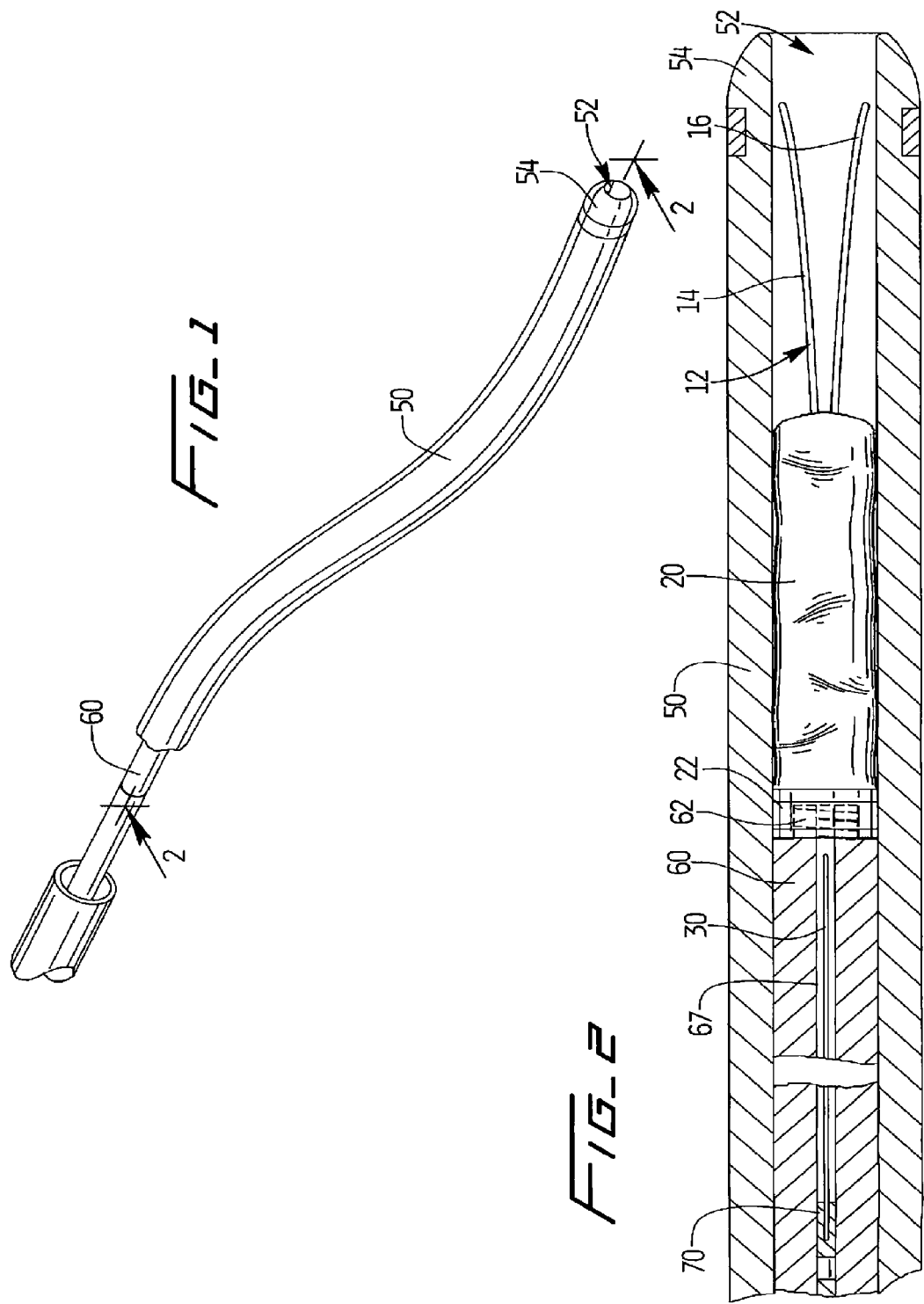

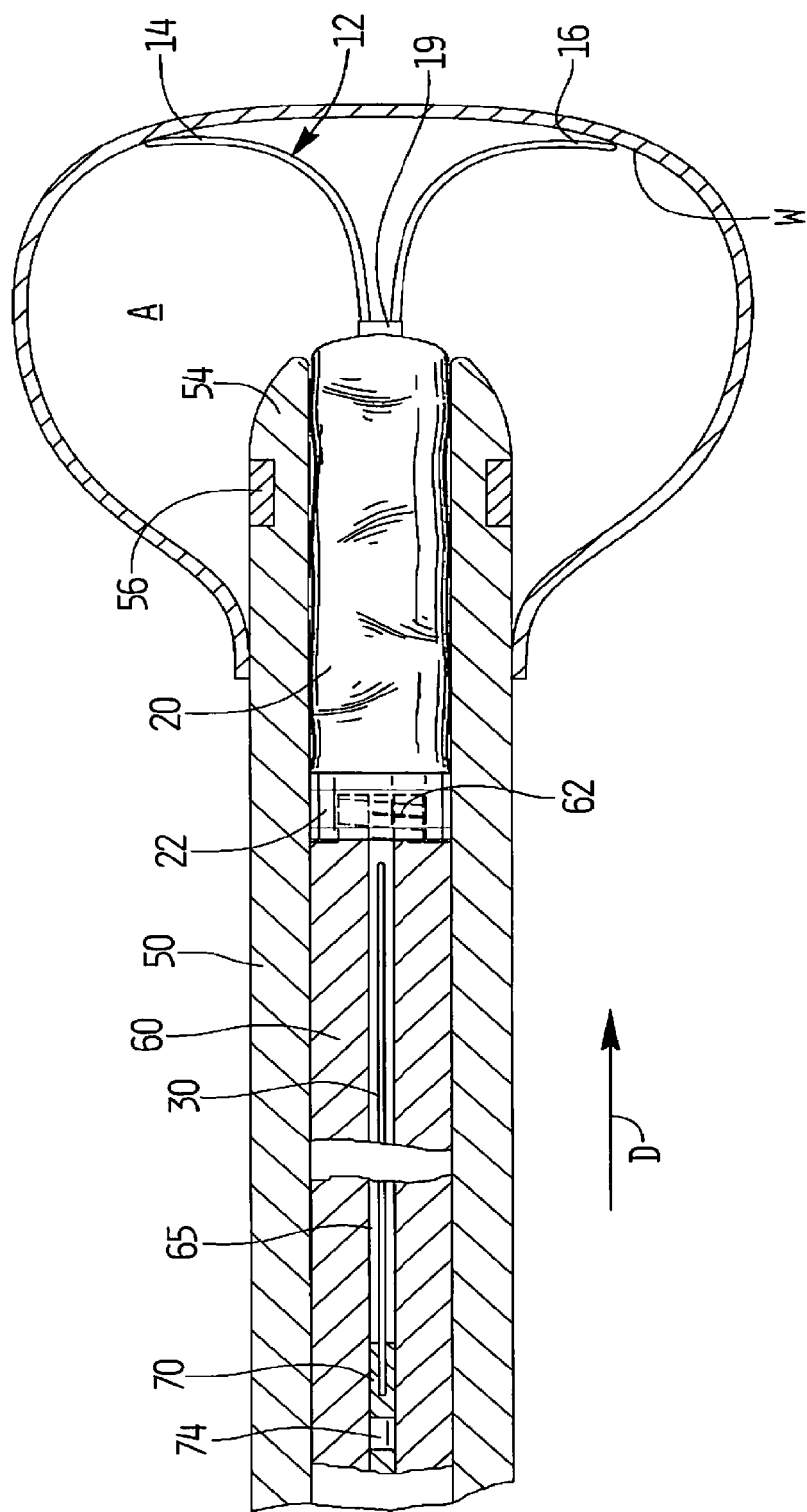

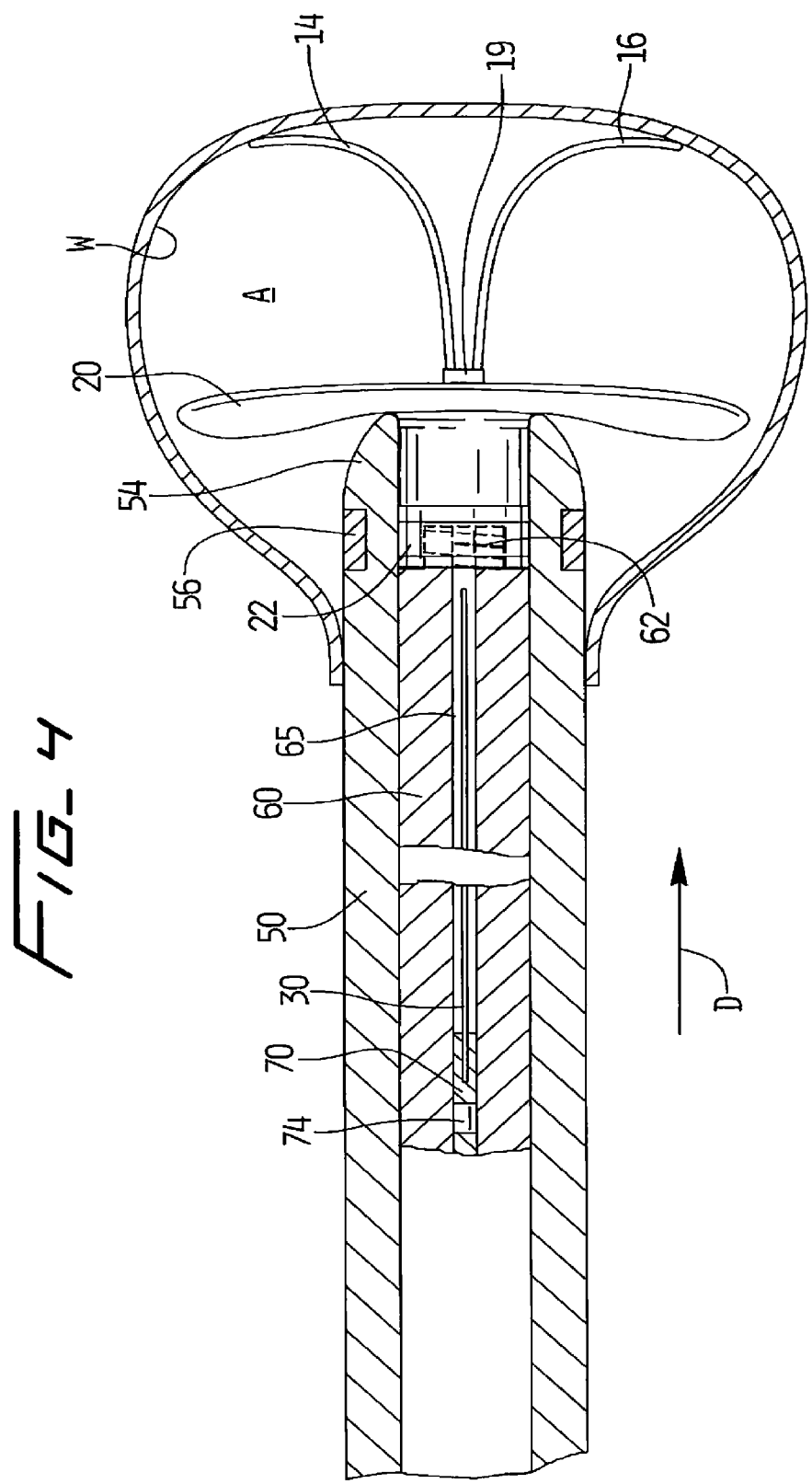

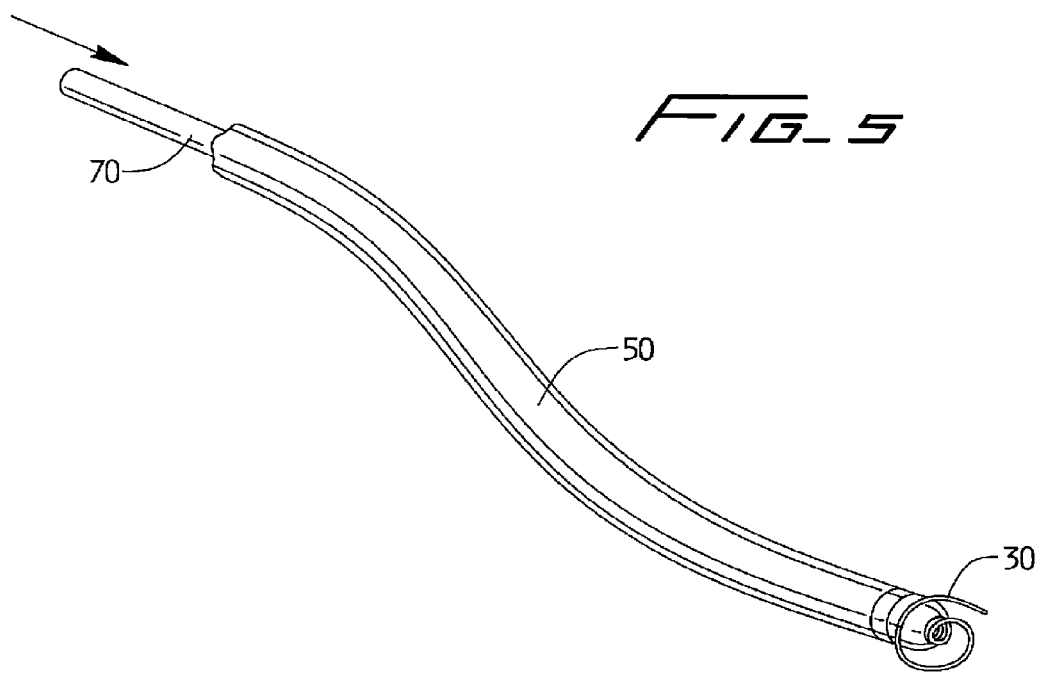
FIG_5
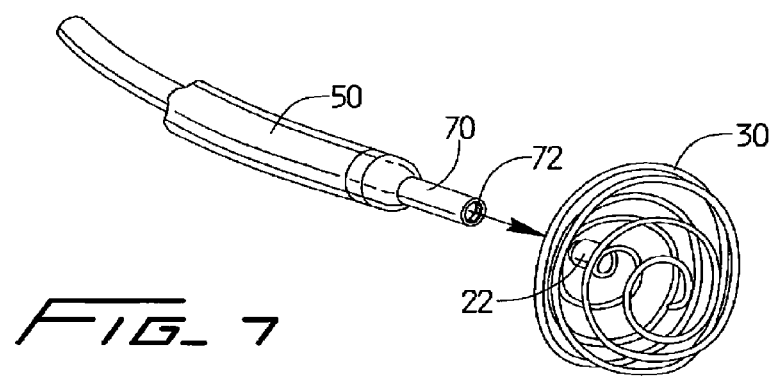
FIG_7

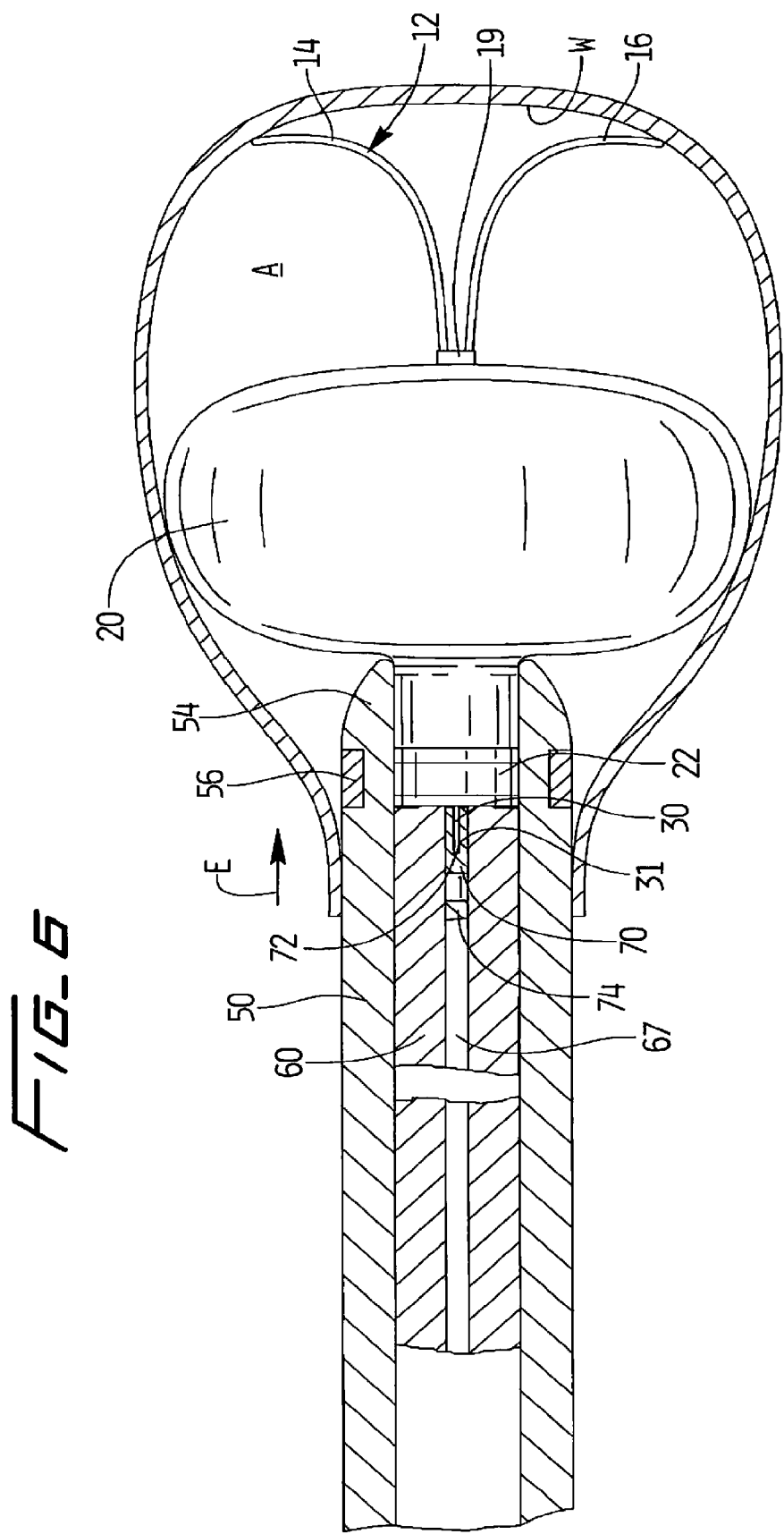

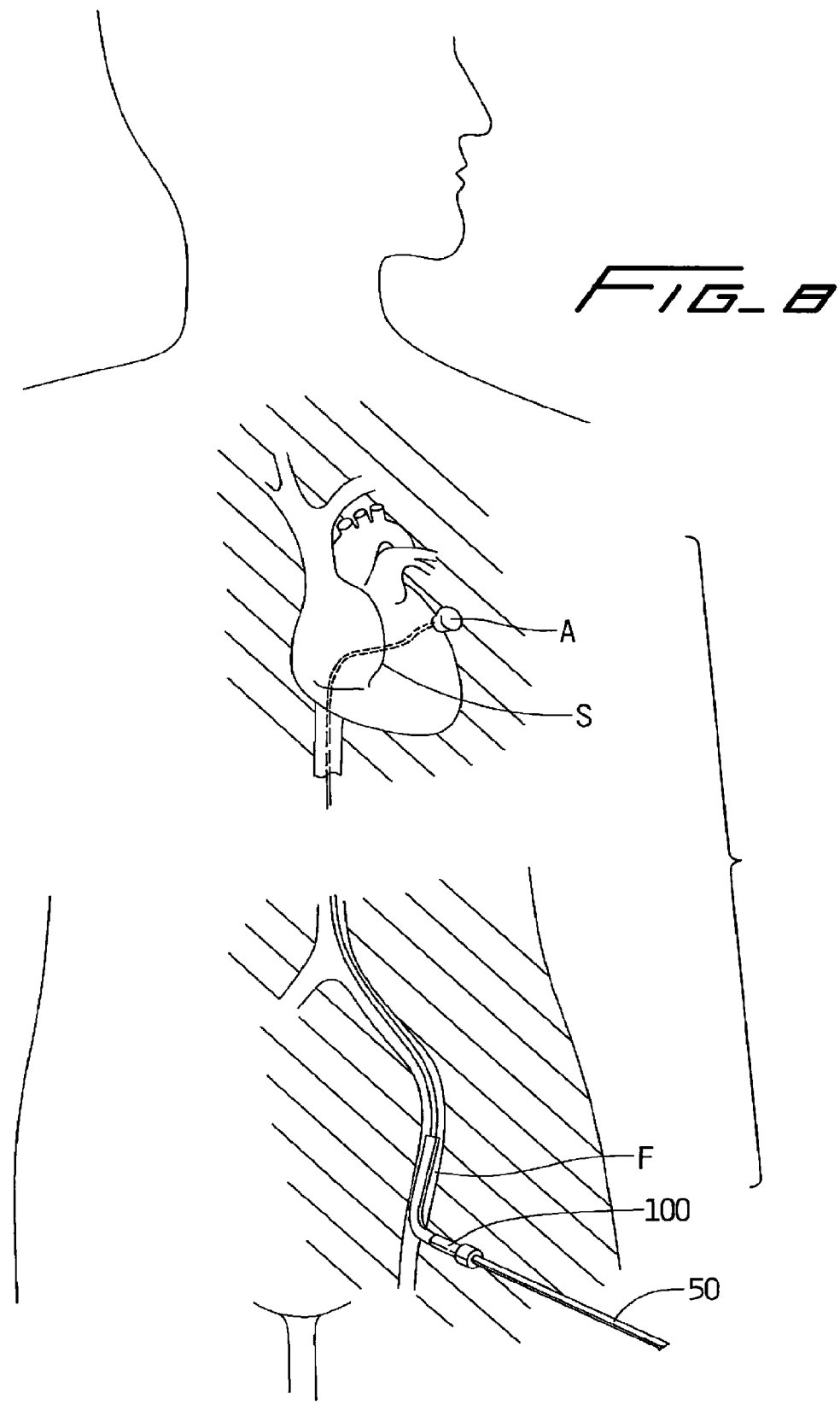

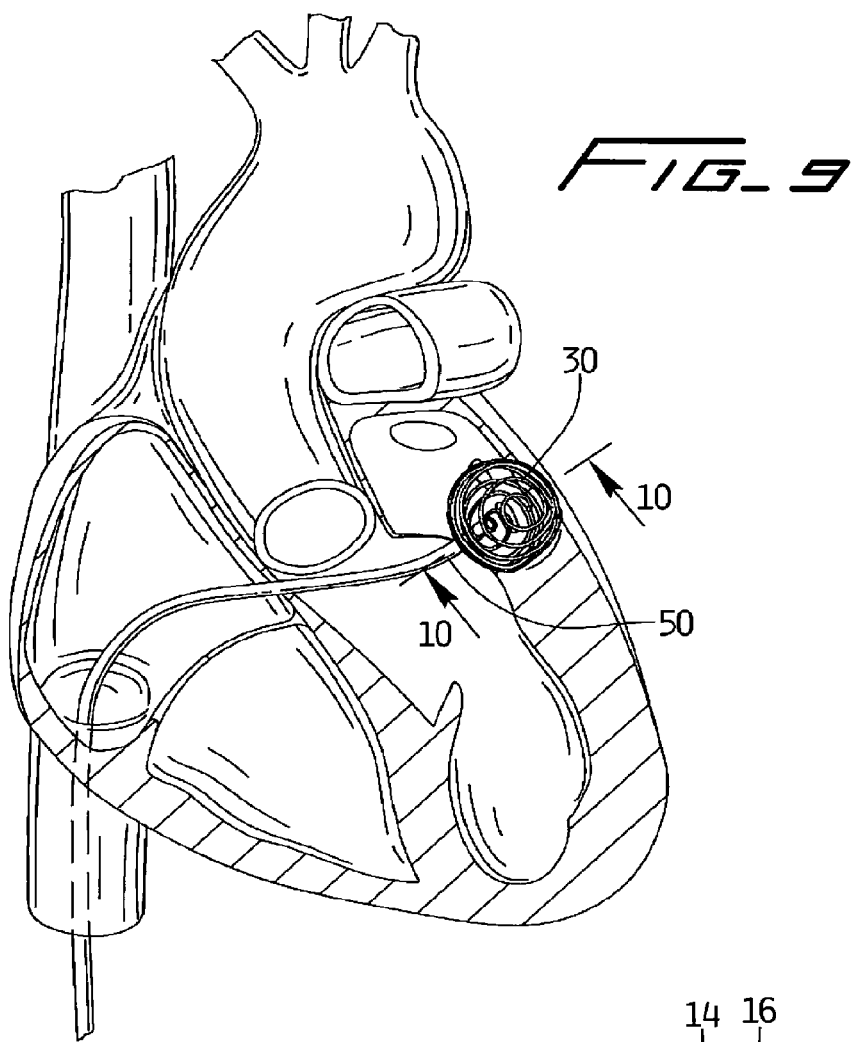
FIG_9
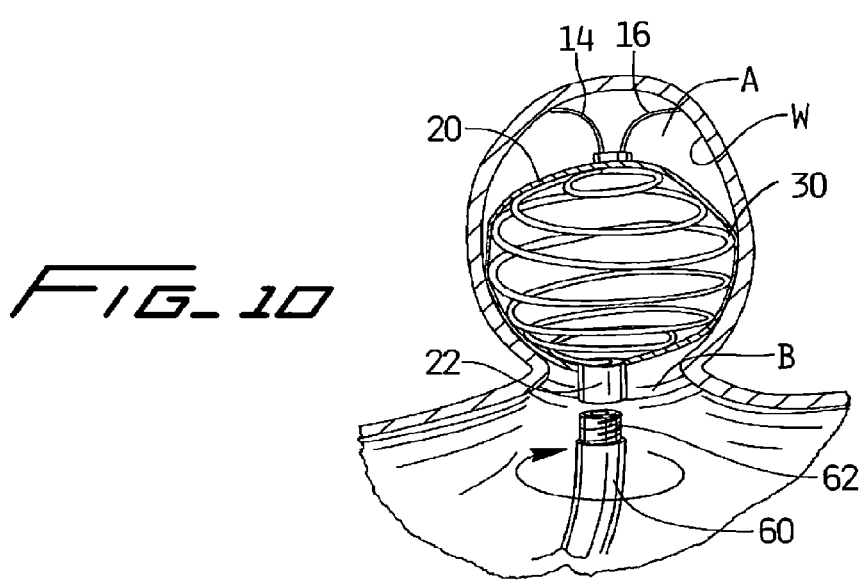
FIG_10

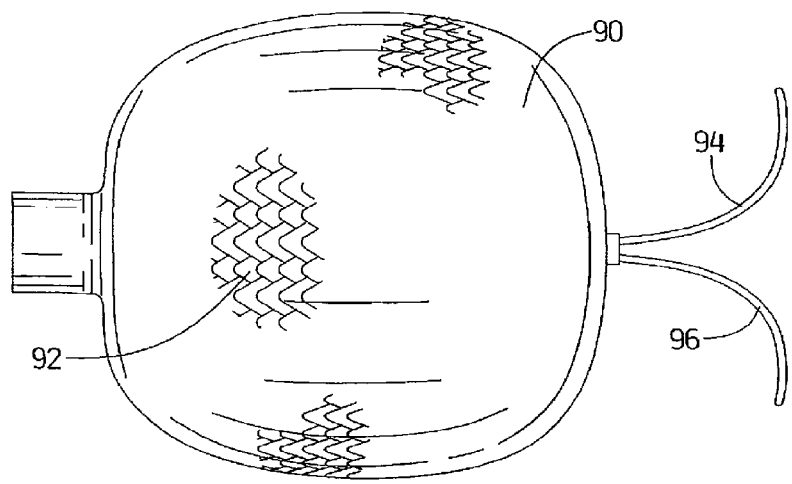
FIG_11
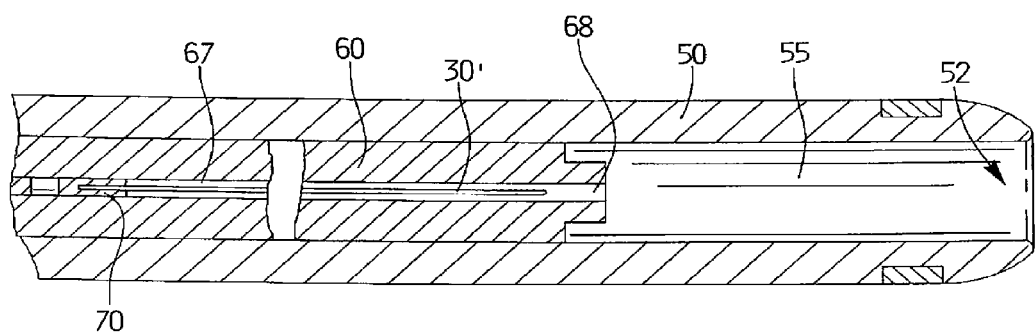
FIG_15

CLOSURE DEVICE FOR LEFT ATRIAL APPENDAGE

This application is a divisional of U.S. application Ser. No. 11/393,539, filed Mar. 30, 2006, now U.S. Pat. No. 8,740,934, which claims priority to U.S. provisional application Ser. No. 60/674,321, filed Apr. 22, 2005. The contents of these applications are incorporated herein by reference.

BACKGROUND

Technical Field

This application relates to a closure device and more particularly to a device for closing the left atrial appendage of the heart.

Background of Related Art

The atrial appendage is a small muscular pouch or cavity attached to the atrium of the heart. The left atrial appendage (LAA) is connected to the wall of the left atrium between the mitral valve and the left pulmonary vein. In proper functioning, the left atrial appendage contracts with the rest of the left atrium during a heart cycle, ensuring regular flow of blood.

Atrial fibrillation is the irregular and randomized contraction of the atrium working independently of the ventricles. This resulting rapid and chaotic heartbeat produces irregular and turbulent blood flow in the vascular system, resulting in the left atrial appendage not contracting regularly with the left atrium. Consequently, the blood can become stagnant and pool in the appendage, resulting in blood clot formation in the appendage. If the blood clot enters the left ventricle it can enter the cerebral vascular system and cause embolic stroke, resulting in disability and even death.

One approach to treatment is the administration of medications to break up the blood clots. However, these blood thinning medications are expensive, increase the risk of bleeding and could have adverse side effects. Another approach is to perform invasive surgery to close off the appendage to contain the blood clot within the appendage. Such invasive open heart surgery is time consuming, traumatic to the patient, increases patient risk and recovery time, and increases costs as extended hospital stays are required.

It is therefore recognized that a minimally invasive approach to closing off the appendage to prevent the migration of blood clots into the ventricle and cranial circulation would be beneficial. These devices, however, need to meet several criteria.

Such minimally invasive devices need to be collapsible to a small enough dimension to enable delivery through a small incision while being expandable to a sufficiently large dimension with sufficient stability to ensure sealing of the appendage is maintained. These devices also need to be atraumatic to ensure the appendage wall isn't perforated which would cause blood leakage into the chest cavity. Further, the size of the appendage can vary among patients and therefore the devices need to be expandable to the appropriate size to close off the appendage. Insufficient expansion comparative to the appendage size could leave a gap large enough for blood clot migration; over expansion could damage the appendage wall.

There have been several attempts in the prior art to provide minimally invasive appendage closure devices. For example, in U.S. Pat. No. 6,488,689, a capture loop or clip is placed around the appendage to hold the appendage closed. These devices can be traumatic to the vascular structure. The Amplatzer occluder marketed by AGA Medical, provides for stent like expansion within a balloon. However, the diameter of expansion is not controllable and the collapsed configuration is relatively large, disadvantageously increasing the profile for insertion. In U.S. Pat. No. 6,152,144, an occluding member having an outer rim and a thin mesh barrier to provide a seal is placed at the opening of the appendage. Radially extending shape memory members extend from the shaft to anchor the device. An expandable anchoring member is also disclosed. In another embodiment, an occlusive coil having a random configuration is placed in the appendage to induce clot. U.S. Pat. Nos. 6,551,303 and 6,652,555 disclose a membrane placed across the ostium of the atrial appendage to prevent blood from entering. Various mechanisms such as shape memory prongs, anchors, springs and struts function to retain the membrane. These devices, however, suffer from various deficiencies and fail to satisfy the size, stability and versatility criteria enumerated above.

Therefore, there is a need for an improved closure device for the left atrial appendage which will effectively block blood clot migration, remain securely retained within the appendage, have a reduced delivery profile to minimize the surgical incision and facilitate passage through the vascular system, and accommodate appendages of different lengths and diameters.

SUMMARY

The present invention overcomes the problems and deficiencies of the prior art. The present invention provides a device for closing a left atrial appendage of a patient comprising a containment member having a first configuration for passage into the left atrial appendage and a second larger configuration, a wire movable into the containment member in situ to expand the containment member in the atrial appendage to the second configuration, and at least one retaining leg to secure the containment member in the left atrial appendage.

Preferably, the wire is composed of shape memory material, is retained in a straighter position during delivery and forms a coil shape in the containment member to expand the containment member.

In one embodiment, multiple discrete wires are movable into the containment member to control the extent of expansion of the containment member. In one embodiment, the containment member is removably connected to a pusher by a screw thread.

In the preferred embodiment, the retaining leg is composed of shape memory material movable between a straighter position for delivery and a second position for engaging a wall of the left atrial appendage. In one embodiment, the at least one retaining leg comprises two legs extending in different directions and in the second position both legs engage the wall of the left atrial appendage.

In an alternate embodiment, the containment member contains a roughened outer surface to engage a wall of the appendage to retain the containment member within the appendage. This roughened surface can be in addition to or instead of the at least one retaining leg.

The present invention also provides a system for closing a left atrial appendage comprising:
 a closure device having a containment member and a wire movable into the containment member to expand the containment member: and
 a delivery system having a delivery tube, a first pusher for advancing the containment member into the left atrial appendage, and a second pusher for advancing the wire from the delivery tube into the containment member.

In a preferred embodiment, a retention member extends from the containment member to engage tissue to secure the containment member. Preferably, the containment member and the wire are in a collapsed position within the delivery tube for delivery and expand to a larger dimension when delivered from the delivery tube, with the wire expanding to a coiled configuration within the containment member to expand the containment member.

In one embodiment, the first pusher is removably attached to the containment member. In one embodiment, the second pusher has a first radiopaque marker and the delivery tube has a second radiopaque marker, the first and second markers coming into substantial alignment to indicate to the user completion of advancement of the second pusher.

In one embodiment, multiple discrete wires are advanceable into the containment member. In such embodiment, after the first wire is ejected into the containment member, a second wire can be loaded in the device and movable by the second pusher (or loaded with a new pusher) into the containment member to further expand the member.

The present invention also provides a method for closing a left atrial appendage comprising:
  providing a containment member and a retaining member for delivery to the left atrial appendage;
  delivering the containment member in a reduced profile position to the left atrial appendage; and
  advancing a wire into the containment member in situ to expand the containment member to block the opening of the left atrial appendage, the retaining member securing the containment member within the appendage.

The method preferably further comprises the step of releasing the retaining member, wherein the retaining member is distal of the containment member so the step of releasing the retaining member occurs prior to expansion of the containment member. Preferably, the step of releasing the retaining member enables the retaining member to move toward a shape memorized configuration. The step of advancing the wire into the containment member preferably enables the wire to move toward a shape memorized configuration within the containment member.

The method may further comprise the step of detaching the containment member from a portion of a delivery instrument by unscrewing the containment member from the delivery instrument.

BRIEF DESCRIPTION OF THE DRAWINGS

Preferred embodiment(s) of the present disclosure are described herein with reference to the drawings wherein:

FIG. 1 is a broken perspective view of a first embodiment of the left atrial appendage closure device of the present invention;

FIG. 2 is a longitudinal cross-sectional view taken along line 2-2 of FIG. 1 showing the closure device in the collapsed position for delivery to the surgical site;

FIG. 3 is a cross-sectional view similar to FIG. 2 showing deployment of the clip (retention leg) of the closure device in the left atrial appendage;

FIG. 4 is a cross-sectional view similar to FIG. 2 showing deployment of the clip and the collapsed bag (containment member) of the closure device in the left atrial appendage;

FIG. 5 is a perspective view illustrating the pusher partially advancing the wire component of the closure device from the delivery tube, the bag and clip (and anatomy) not shown for clarity;

FIG. 6 is a cross-sectional view similar to FIG. 2 showing the pusher for the wire further advanced to move more of the wire into the bag to expand the bag;

FIG. 7 is a perspective view of the distal portion of the pusher and delivery tube illustrating the wire deployed from the tube to assume the coiled configuration, the bag and clip (and anatomy) not shown for clarity;

FIG. 8 illustrates insertion of the closure device via a femoral and trans-septal approach to access the left atrial appendage;

FIG. 9 illustrates the wire of the closure device fully deployed in the left atrial appendage, (the bag and clip are removed for clarity);

FIG. 10 is a view along line 10-10 of FIG. 9 illustrating the closure device fully deployed in the left atrial appendage and further showing the detachment of the pusher from the closure device (a portion of the bag is removed for clarity);

FIG. 11 is a perspective view of an alternate embodiment of the bag of the present invention having a roughened outer surface;

FIG. 15 is a cross-sectional view illustrating the second wire positioned in the delivery tube.

DETAILED DESCRIPTION OF PREFERRED EMBODIMENTS

Figure 12:
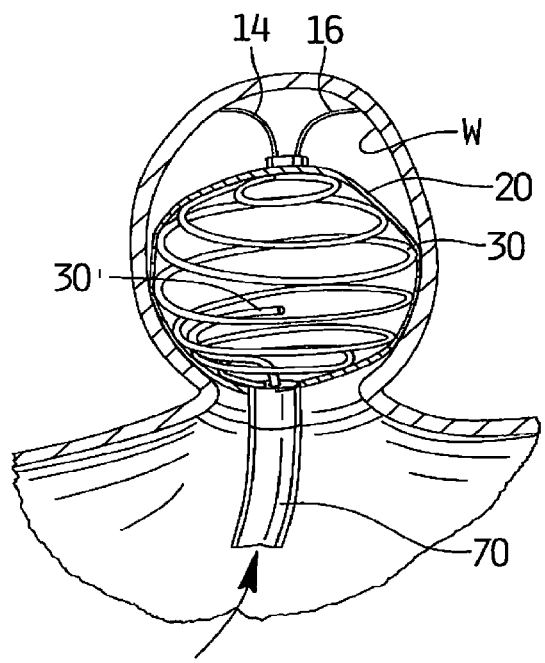
FIG. 12 is a perspective view of the closure device positioned in the left atrial appendage and illustrates partial advancement of a second wire into the bag.

Referring now in detail to the drawings where like reference numerals identify similar or like components throughout the several views, the present invention provides a closure device for closing the left atrial appendage ("LAA") and a delivery system for placement of the closure device. With initial reference to FIGS. 2 and 6 which show the closure device in the delivery and deployed configurations, respectively, the closure device includes a clip component 12 and a bag component 20. The bag 20 is expandable within the appendage and is retained by the clip 12 which engages the interior wall of the appendage. The closure device further includes a wire component 30 having a coil shape as shown in FIG. 7. The bag 20 forms a containment member for the wire 30. That is, the wire 30 is advanced into the bag 20 in situ as described in detail below to expand the bag 20 to prevent passage through the opening into the appendage. The expanded bag 20 thereby blocks the LAA opening to prevent migration of blood clots from the appendage.

The delivery system for the closure device includes a catheter or delivery tube 50, a pusher 60 for advancing the bag (containment member) 20 and attached clip 12 into the appendage A, and a pusher 70 for advancing the wire 30 into the bag 20. Pusher 60 has an axial lumen 67 to slidably receive pusher 70. The pusher 60 is preferably separable from the bag 20 to separate the pusher after the bag 20 has been properly placed at the desired surgical site in the appendage. Such detachment is preferably achieved by the provision of a screw thread 62 at the distal end of pusher 60 which threads into support 22 which is connected to a proximal end of the bag 20. Thus, the cylindrical support 22 has internal screw threads which threadedly mate with the external threads of pusher 60. Axial movement of pusher 60 advances the bag 20 due to attachment to support 22. Rotational movement of pusher 60 unscrews pusher 60 from support 22. Other ways to removably connect the pusher to the bag are also contemplated. These detachment systems would also provide the option to reposition the closure device or remove it if necessary, (e.g., in the case of perforation or tamponade).

The clip component 12 functions as a retaining member and includes two clip legs 14, 16 extending distally from bag 20, preferably in opposite directions. These retaining legs 14, 16 are dimensioned and configured to engage the appendage wall W to help retain the closure device in position. Preferably the clip legs 14, 16 are composed of shape memory material, such as Nitinol, with an austenitic shape memorized position illustrated in FIG. 3. Materials other than Nitinol or shape memory are also contemplated. The clip legs 14, 16 are maintained in a substantially straightened softer martensitic configuration within the catheter 50 for delivery as shown in FIG. 2. Cold saline can be injected during delivery to maintain the legs 14, 16 in this martensitic condition to facilitate exit from the distal opening 52 at the distal end portion 54 of catheter 50. When legs 14, 16 exit the delivery tube 50, they are warmed by body temperature and move radially in different (e.g., opposite) directions toward their illustrated memorized curved position as shown in FIG. 3. As an alternative to two clip (retention) legs, a single clip leg or more than two clip legs could be provided.

The bag can be composed of a variety of materials, such as Gore-Tex, PFTE, polyethylene, SIS, bovine of equine pericardium, etc. A non-thrombogenic surface is desirable. The bag 20 is in the collapsed configuration within catheter 50 for delivery as shown in FIG. 2; it is expanded by the coiled shape wire 30 to the configuration of FIG. 10. The bag could also be made of a tissue-like substance which could permit endothelization and incorporation.

FIG. 11 illustrates an alternate embodiment of the bag. Bag 90 has a roughened surface, such as a series of scales 92, designed to engage the appendage wall W and secure the bag. The bag 90 is shown used with clip legs 94, 96 (preferably identical to clip legs 14, 16); however, it is also contemplated that the roughened surface could be configured to provide sufficient retention such that clip legs need not be provided.

The wire 30 is preferably composed of shape memory material, such as Nitinol, with an austenitic coil shaped memorized position illustrated in FIG. 7. Materials other than Nitinol are also contemplated. When advanced from the delivery tube 50, the wire 30 is warmed by body temperature and moves from its elongated substantially straight delivery configuration of FIG. 2 to its memorized configuration within bag 30 (FIGS. 7 and 10). That is, wire 30 is maintained in this substantially straightened softer martensitic configuration within the catheter to reduce its profile (overall transverse dimension) for delivery. Cold saline can be injected during delivery to maintain the wire 30 in this martensitic condition to facilitate exit from the distal opening 52 at the distal end portion 54 of catheter 50 by reducing frictional contact with the internal wall of catheter 50.

The method of placement of the closure device of the present invention will now be described for closing a left atrial appendage. A delivery catheter 50 is inserted through an introducer sheath 100 in the femoral vein F and advanced through the septum S to access the left atrial appendage A as shown in FIG. 8. For insertion, the bag 20, clip 12 and wire 30 are all in the collapsed position. That is, as shown in FIG. 2, the clip legs 14, 16 are in a substantially straight position. The wire 30 is also in a substantially straight position and bag 20 is collapsed in a longitudinally elongated orientation. This provides for a reduced profile insertion configuration.

In the first step, pusher 60 is advanced distally, (e.g., by a handle (not shown) or other mechanism) at a proximal end of the catheter 50) in the direction of arrow D of FIG. 3. Distal advancement of pusher 60 advances legs 14 and 16 from the catheter 50 as the distal end 62 of pusher 60 is attached to the proximal end of bag 20 via support 22 and the clip legs 14, 16 are attached to the distal end of the bag 20. As the legs 14, 16 are exposed, they are warmed by body temperature and return toward their shape memorized deployed position as shown in FIG. 3 to engage the appendage wall W. The extent they return to their fully memorized position will depend on the size of the appendage and the thickness of the tissue.

Next, pusher 60 is further advanced in the direction of arrow D of FIG. 4 to advance bag 20 from catheter 50 into appendage A. The bag 20 remains at this point in the collapsed configuration. Note that the bag 20 is still attached to pusher 60.

Next, pusher 70 is advanced distally in the direction of arrow E of FIG. 6 so engagement by distal end 72 with the proximal end 31 of wire 30 will force wire 30 into the bag 20 positioned in the appendage A. As the wire 30 exits the catheter 50 and enters the bag 20 within appendage A, it is warmed by body temperature and moves toward its shape memorized coiled configuration. This coiled configuration expands bag 20. FIG. 6 illustrates the bag 20 in an expanded configuration due to the expansion of the coil but not yet fully expanded because pusher 70 has not yet been fully advanced to fully deploy wire 30. FIGS. 5 and 7 illustrate the movement of the wire from initial exit from catheter 50 to expansion into its full coiled configuration. The bag 20 is not shown in these drawings for clarity. The anatomy is also not shown for clarity. FIGS. 9 and 10 illustrate the fully deployed position of the closure device with portions of bag 20 removed for clarity.

As can be appreciated, expansion of the wire (coil) 30 expands the bag 20 to fill the appendage space to block the migration of blood cells from the appendage. The engagement of clip legs 14 and 16 with the appendage wall W provides addition retention of bag 20.

Note that in the preferred illustrated embodiment, the pusher 70 has a radiopaque marker 74 which can align with the radiopaque marker 56 on the catheter 50. This will provide a visual indication to the user that the pusher 70 has completed its travel and the wire coil 30 has been inserted as the two markers align and provide a relatively large solid area for imaging. This will occur on full advancement of pusher 70 (to a position distal of FIG. 6). A radiopaque marker 19 is also preferably provided at the base of legs 14, 16 adjacent the bag 20 for imaging.

After full insertion of the wire 30 into the bag 20, pusher 60 is rotated to unscrew thread 62 from support 22 to disconnect the bag 20. The pusher 60 along with the catheter 50 can then be withdrawn, leaving the closure device in place as shown in FIG. 10. Preferably, the bag will be positioned at the opening to the appendage and may even extend slightly past the opening into the atrium. As can be appreciated, the expanded bag 20 blocks the opening B in the appendage A to prevent migration of thrombus from the appendage A into the atrium and left ventricle.

Different lengths or expansions of the wire 30 can be provided depending on the size of the appendage and how much is needed to expand or fill the bag. Thus, a customized device could be provided. The size of the appendage can be determined, and then the length and diameter of bag expansion can be adjusted accordingly. This is illustrated for example, in FIG. 12-15.

As shown in FIG. 12, a second wire 30' is advanced by the pusher in the direction of the arrow into bag 20. The wire 30' can be loaded in the device and advanced by pusher 70 by withdrawing pusher 70 from lumen 67 of pusher 60 and then inserting the wire 30' and pusher 70 into the lumen 67. This is shown in the embodiment of FIG. 15. Note the pusher 70 is reloaded in lumen 67 and can be advanced to move wire 30' through opening 68 and through the catheter region 55 (which no longer has a bag or clip since they were already deployed). Alternatively, pusher 60 can first be advanced to the distal opening 52 in catheter 50 so that the wire 30' will exit opening 68 at the distal opening 52 when advanced by pusher 70. Alternately, instead of utilizing the same pusher, a new pusher can be loaded with the wire within lumen 67 of pusher 60 after the pusher 70 for wire 30' is withdrawn.

Figure 13:
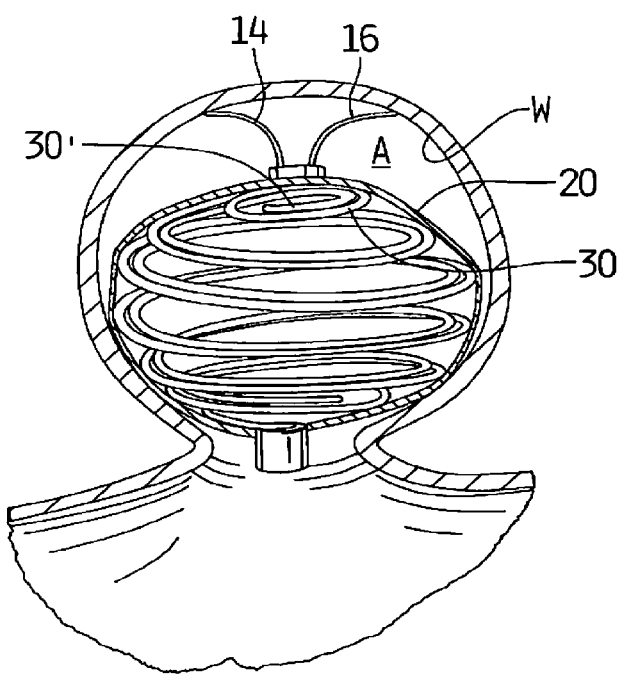
FIG. 13 is a perspective view illustrating the second wire fully advanced into the bag to further expand the bag.

As can be appreciated, advancement of the wire 30' further fills bag 20 to increase its diameter to better fill the appendage A (see FIG. 13). Alternatively, the additional wire(s) can be used to increase the length of the bag. The customized device also enables wire coils of different sizes to be selectively preloaded in the device. After determining the appendage size, the desired coil size can be selected as well as the number of wires (coils). Since the wire is delivered in the straightened configuration, selection of a coil with a larger transverse dimension when expanded would not affect incision size nor increase delivery profile, thereby, keeping delivery profile at a minimum.

Figure 14:
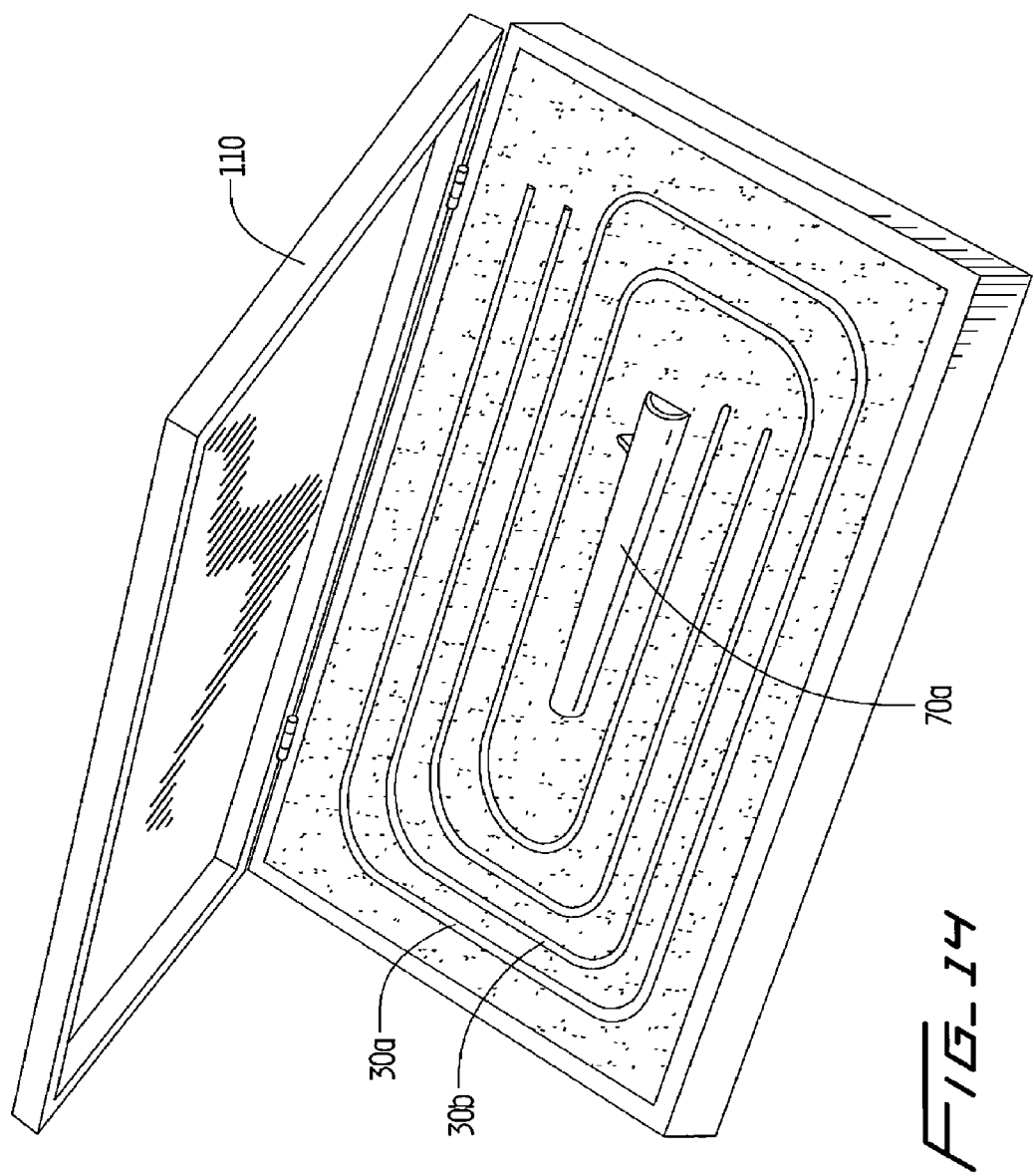
FIG. 14 is a perspective view of a kit containing a pusher and two wires.

The kit of FIG. 14 provides an example of two discrete wires. The wires shown are different sizes with wire 30a being longer than wire 30b. Also, in an alternate embodiment, the kit could contain additional discrete wires of the same or different size to provide a customized device for the left atrial appendage. A new pusher 70a is also illustrated in the kit. The pusher 70a has a tab 72a, and is loaded into the lumen of pusher 60 as described above. The tab 72 facilitates manual advancement of the pusher 70a. The kit includes hinged cover 110.

As can be appreciated, although described for closing the left atrial appendage of the heart, the closure device can also be used to embolize other conduits such as blood-vessels, ureters of fistulas.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A method for closing a left atrial appendage comprising:
providing a containment member and a retaining member extending distally from the containment member for delivery to the left atrial appendage, the containment member and retaining member positioned in a delivery instrument having a first pusher and a second pusher, and a wire positioned proximal of the containment member so that a distal end of the wire is proximal of the proximal end of the containment member, the first pusher having a first lumen and a connecting structure for connection of the containment member, the first lumen receiving the second pusher and the wire terminating at a distal end within the first lumen;

advancing the first pusher distally to advance the retaining member and the containment member distally out of the delivery instrument to deliver the retaining member to the left atrial appendage and the containment member in a reduced profile position to the left atrial appendage, the retaining member attached to a distal end of the containment member and having distally directed legs extending in a direction away from the containment member and movable radially within the left atrial appendage, the wire remaining outside the containment member as the containment member is advanced within the left atrial appendage; and advancing the second pusher distally to advance the wire distally into the containment member in situ to expand the containment member to block the opening of the left atrial appendage, the retaining member securing the containment member within the appendage.

2. The method of claim 1, further comprising the step of releasing the retaining member from the delivery instrument, the step of releasing the retaining member occurs prior to the expansion of the containment member.

3. The method of claim 2, wherein the step of releasing the retaining member enables the retaining member to move toward a shape memorized configuration.

4. The method of claim 1, further comprising the step of detaching the containment member from the first pusher.

5. The method of claim 4, wherein the step of detaching the containment member comprises the step of unscrewing the containment member from the first pusher.

6. The method of claim 4, wherein advancement of the first pusher initially releases the retaining member to move to an expanded position and subsequent movement of the first pusher releases the containment member from the delivery instrument.

7. The method of claim 1, wherein the step of advancing the wire into the containment member enables the wire to move toward a shape memorized configuration within the containment member.

8. The method of claim 1, wherein the first pusher and the second pusher are coaxial.

9. The method of claim 8, wherein the second pusher includes a radiopaque marker to provide a visual indication that the second pusher has traveled to advance the wire into the containment member.

10. The method of claim 1, wherein the legs are maintained in a substantially straightened configuration for delivery and when delivered move radially in different directions.

11. The method of claim 1, wherein the wire is a coiled shaped wire.

12. The method of claim 1, wherein the containment member has a roughened surface to engage the appendage wall.

13. The method of claim 1, wherein the wire is in a substantially straightened positioned during delivery.

14. The method of claim 1, wherein the retaining member is initially advanced from the delivery instrument while the containment member remains within the delivery instrument and the containment member is detached from the first pusher after the second pusher has advanced the wire into the containment member.

15. The method of claim 1, further comprising the step of advancing a second wire into the containment member in situ.

16. The method of claim 15, wherein the step of advancing the second wire includes withdrawing the second pusher and inserting a second wire in a lumen of the first pusher.

17. The method of claim 1, wherein during delivery the retaining member and the wire are in a substantially straightened configuration.

\* \* \* \* \*